United States Patent [19]
Wallshein

[11] 4,186,488
[45] Feb. 5, 1980

[54] ORTHODONTIC BRACKET WITH MULTI-LAYER BASE

[76] Inventor: Melvin Wallshein, 8645 Bay Pkwy., Brooklyn, N.Y. 11214

[21] Appl. No.: 850,718

[22] Filed: Nov. 11, 1977

[51] Int. Cl.² .............................................. A61C 7/00
[52] U.S. Cl. ........................................................ 433/8
[58] Field of Search .............................. 32/14 A, 14 C

[56] References Cited
U.S. PATENT DOCUMENTS

| | | | |
|---|---|---|---|
| 3,250,003 | 5/1966 | Collito | 32/14 A |
| 3,464,112 | 9/1969 | Silverman et al. | 32/14 A |
| 3,477,128 | 11/1969 | Andrews | 32/14 A |

*Primary Examiner*—Robert Peshock
*Attorney, Agent, or Firm*—Frishauf, Holtz, Goodman and Woodward

[57] ABSTRACT

An orthodontic bracket comprises a bracket member having a base and an arch wire receiving opening in a surface of the bracket; and a mounting layer secured to the base of the bracket member and adapted to be mounted to a tooth or the like. At least one of the bracket member and mounting layer is made of resilient material.

11 Claims, 13 Drawing Figures

ORTHODONTIC BRACKET WITH MULTI-LAYER BASE

This invention relates to orthodontic brackets, and more particularly to orthodontic brackets having multi-layer bases. The layers of the base are preferably laminated on each other.

Presently available orthodontic brackets are generally made from metal or hard plastic. The brackets are typically one-piece brackets which are designed to be either mounted to a tooth via a metallic band or to be directly adhered to a surface of a tooth so as to transmit orthodontic forces to the tooth.

The object of the present invention is to provide an orthodontic bracket with a composite or layered base structure, at least one layer of the composite base structure being of elastic material so as to provide a resilient interconnection between the orthodontic bracket and the tooth.

SUMMARY OF THE INVENTION

In accordance with the present invention, an orthodontic bracket comprises a bracket member having a base and an arch wire receiving opening formed in a surface of the bracket; and a mounting layer secured to the base of the bracket and adapted to be mounted to a tooth or the like. At least one of the bracket member and the mounting layer is made of a resilient material.

The mounting layer may be either a simple layer secured to the rear surface of the base of the bracket, or may at least partially encircle portions of the base of the bracket in order to provide a more secure connection therebetween. In an alternative embodiment, the mounting layer may have an inclined surface portion so as to permit the bracket to be mounted to a tooth with an angular orientation relative to the tooth in order to permit applying orthodontic forces to a tooth. The mounting layer may have a flat surface which connects to a bracket, the opposite surface thereof being curved so as to better conform to the surface of a tooth on which the bracket is to be mounted.

In a modified embodiment where the mounting layer is made of resilient material, the mounting layer may comprise a generally ring-shaped structure. This type of construction allows slightly more resilient relative movement between the bracket and a tooth.

An advantage of the arrangement of the present invention is that resilient orthodontic forces may be applied to a tooth via the elastic mounting layer or via an elastic bracket member. Another advantage to the arrangement of the present invention is that a resilient mounting layer enables the bracket to withstand shearing forces, such as those occurring when chewing food, without being broken off from the tooth as sometimes occurs with conventional brackets. Also, a resilient mounting layer will reduce the chances of a bracket, for example a plastic bracket, from being damaged due to forces applied thereto by the patient when chewing food, or the like. The orthodontic forces which may be applied via the elastic or resilient connection of an arch wire to a tooth include a twisting force whereby the bracket tends to twist in a plane parallel to the tooth face, as well as other forces.

While the above discussion was given in connection with applying orthodontic brackets to teeth, a resilient mounting layer may be used in connection with mounting other orthodontic appliances to teeth, such as lingual cleats, rotating buttons, buccal end tubes, lingual arch attachments, etc., to obtain similar advantages.

DETAILED DESCRIPTION

Figure 1:
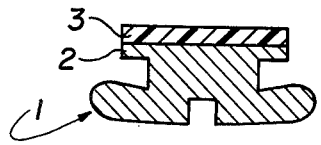
FIG. 1 is a cross sectional view of a first embodiment of the present invention.

Referring to FIG. 1, the first embodiment of the invention comprises an orthodontic bracket member 1 having a base portion 2 which is secured to an elastic layer 3. The elastic layer 3 is adapted to be either directly adhered to a tooth by means of an adhesive or to an orthodontic band which encircles a tooth. The elastic or resilient layer 3 may be connected to a tooth by any of the known conventional adhering materials and methods.

The bracket 1 may be of metal or plastic materials. When made of plastic materials, the bracket may be resilient or non-resilient, as desired, and may be more or less resilient than the elastic base member 3. The elastic base member 3 is adhered to base portion 2 of the bracket by means of, for example, an adhesive.

An advantage of the arrangement of FIG. 1 is that the resilient connection to the tooth via the elastic or elastomeric layer 3 can be used to impart orthodontic forces to a tooth during treatment of a patient. Also, the resiliency of the elastic layer 3 enables an orthodontic force to be more gently applied, as compared with applying the orthodontic force via a bracket which is rigidly connected to a tooth.

Figure 2A:
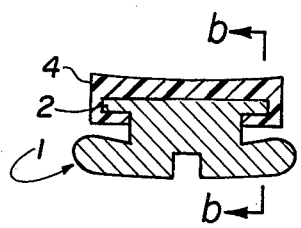
FIGS. 2a and 2b are cross-sectional views of another embodiment of the invention.
Figure 2B:
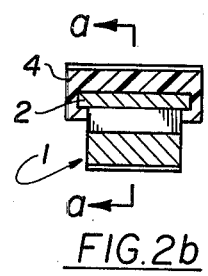

FIGS. 2a and 2b show another form of the invention wherein the elastic layer or member 4 not only is interposed between the base portion 2 of the bracket and the tooth, but also encircles at least a part of the base portion 2 so as to provide greater structural integrity at the connection between the elastic member 4 and base portion 2 of the bracket 1. The elastic portion 4 may be adhered to base portion 2 by means of an adhesive so as to increase the strength of the connection therebetween. Such an adhesive, however, is not absolutely required in the embodiment of FIGS. 2a and 2b. The elastic member 4 may be fabricated separately from the bracket and installed over the base portion 2 by means of stretching same, or it may be directly molded over the base portion 2 of the bracket. Alternatively, the elastic member may be fabricated in the form of a jacket, for example as shown in an enlarged view as member 4' in FIG. 3, which may be slid onto the base portion 2 of the bracket and adhered thereto by means of an adhesive.

Figure 4:
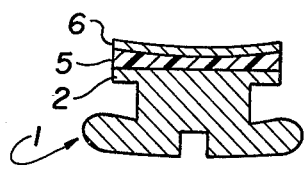
FIG. 4 is a cross-sectional view of a further embodiment of the invention.

FIG. 4 illustrates a further modified embodiment of the present invention which comprises an elastic layer 5 secured, for example by means of an adhesive, to the back of the base portion 2 of the bracket 1, and further comprising a non-resilient layer 6 secured to the free surface of the elastic material 5. In certain instances, this construction may be advantageous. The resulting function is similar to that of the arrangement of FIG. 1.

Figure 5:
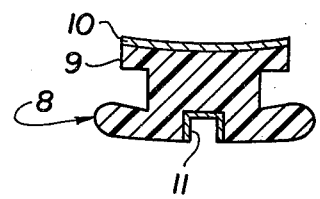
FIG. 5 is a cross-sectional view of yet another embodiment of the invention.

FIG. 5 illustrates a further embodiment of the present invention comprising an elastic bracket 8 having a base portion 9 which has an inelastic layer 10 secured to the rear surface thereof. The elastic bracket 8 may have a liner 11 in the arch wire opening thereof in order to reinforce same, substantially as shown and described in my prior U.S. patent applications, Ser. No. 698,915 filed June 23, 1976 and Ser. No. 782,028 filed Mar. 28, 1977. In this embodiment, a rigid connection may be made to the tooth via the inelastic layer 10, which may be metal, and an elastic coupling between the arch wire and the tooth is provided via the elastic bracket 8.

Figure 6A:
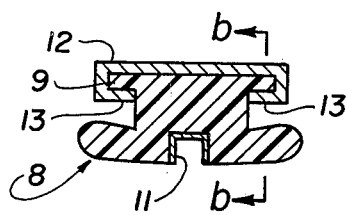
FIGS. 6a and 6b are cross-sectional views of still another embodiment of the invention.
Figure 6B:
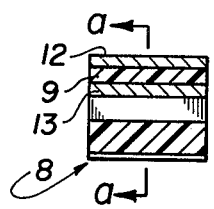

FIGS. 6a and 6b illustrate a modification of the arrangement of FIG. 5 wherein an inelastic layer 12 wraps around (note portions 13) the top and bottom of the base portion 9 of the elastic bracket 8. This arrangement is similar to that of FIG. 2 except that the inelastic and elastic materials are reversed, and except that the inelastic layer 12 does not wrap around the sides of the bracket 8—compare FIGS. 2a and 6b.

Figure 3:
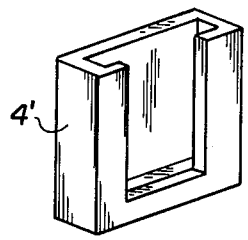
FIG. 3 is a perspective view of an elastic member for use in the present invention.

The inelastic member 12, which may be of metal, shown in FIG. 6 may be prefabricated so as to be similar in shape to the member 4' of FIG. 3 and the elastic bracket may be slid therein. Alternatively, the inelastic layer 12 may be formed around a preformed elastic bracket by bending. With this method of manufacture, the front portions 13 of inelastic member 12 may be crimped or otherwise over-bent so as to pierce or otherwise pressingly engage the elastic base member 9 of the elastic bracket 8 so as to provide a high degree of structural integrity between the two members. As mentioned above with respect to FIG. 5, a liner 11, preferably made of hard, inelastic material such as metal, can be used in the arch wire opening of the bracket so as to protect the bracket and to provide a proper receptacle for an arch wire, or the like.

Figure 7:
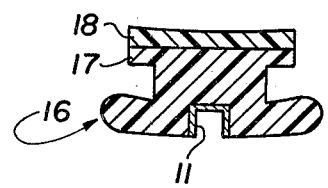
FIG. 7 is a cross-sectional view of an embodiment of the invention using resilient or elastic material for both the bracket and connecting layer.

FIG. 7 illustrates another composite bracket of the invention comprising an elastic bracket 16 and an elastic mounting layer 18 adhered or otherwise secured to the base 17 of the bracket 16. The elastic materials of the bracket 16 and mounting layer 18 may be the same or different. Preferably, the mounting layer 18 is more resilient than the bracket 16. A hard liner 11 may be used in the arch wire receiving opening of the bracket.

Figure 8:
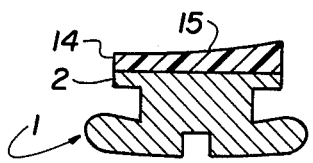
FIG. 8 illustrates a modification of the embodiment of FIG. 1.

FIG. 8 illustrates a modified arrangement of the invention wherein the elastic member 14 is adhered to a bracket 1, the elastic member 14 having an inclined surface 15 so that the bracket may be installed on a tooth with an angular orientation relative to the tooth. This not only permits brackets to be custom-mounted to teeth, but also permits the bracket, via the elastic member 14, to be used to apply a positive orthodontic force to a tooth, for example a rotational force. The inclined mounting surface can be applied to any of the illustrated embodiments.

Figure 9:
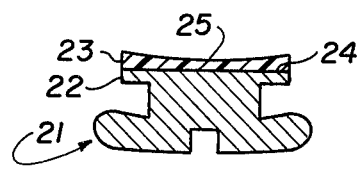
FIG. 9 illustrates a further modification of the present invention.

FIG. 9 illustrates a further modified arrangement of the present invention wherein the elastic member 23 has a substantially flat surface 24 which is secured to the base portion 22 of a bracket 21. The elastic member 23 further has a curved surface 25 which is adapted to be mounted to a tooth, or an orthodontic band, the curvature of the surface 25 being such as to conform generally to the curvature of a tooth on which the bracket is to be mounted. This construction enables the bracket 21 to be easily manufactured, the curvature being added only to the elastic member 23.

Figure 10:
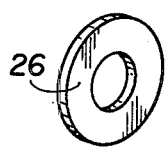
FIG. 10 illustrates a resilient mounting layer according to another embodiment of the present invention.

FIG. 10 illustrates a modified ring-shaped elastic member which may replace any of the aforementioned elastic members, and which is especially suited for use with a bracket having a round base portion 2. The ring-shaped elastic member 26 is particularly advantageous in that it provides a slightly greater resiliency when mounting a bracket to a tooth.

Figure 11:
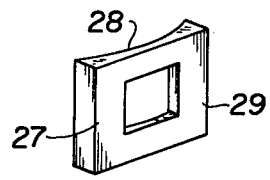
FIG. 11 illustrates a still further resilient mounting layer according to the present invention.

FIG. 11 shows a ring-shaped elastic member 27 which is generally rectangular and which has a generally rectangular inner opening. The rear surface 28 of the ring member 27 may be curved, similar to surface 25 in FIG. 9, to facilitate mounting. Surface 29 of the member 28 is adapted to be secured to the base portion of a bracket, such as base portion 22 of FIG. 9.

The elastic mounting members of FIGS. 1-9, all of which are solid members, may be replaced by ring-shaped members so as those shown in FIGS. 10 and 11, or other elastic members having variously shaped cut-out portions.

The invention has been described above with specific reference to edgewise brackets. However, it is equally applicable to all other types of brackets and their use is within the present inventive concept, as claimed. Moreover, the elastic or resilient mounting layers could be used with appliances other than orthodontic brackets to provide similar advantages.

A typical adhesive which may be used to secure the various layers together and to secure the appliance to a tooth is a cyanoacrylate adhesive, such as Eastman 910 adhesive. The elastic or resilient layers, such as layers 3,4 etc. may be made from elastomeric materials such as rubber While the invention has been described above with respect to specific embodiments, it should be clear that various modifications and alterations may be made within the scope of the invention as set forth in the appended claims. For example, the brackets of FIGS. 1, 2, 4, 8 and 9 may be plastic or metal, resilient or non-resilient, as desired. Any of the bracket arrangements can be provided with liners, such as liner 11, in their arch wire receiving openings, as shown and described in my prior U.S. patent applications, Ser. Nos. 698,915 and 782,028. Additionally, the rear mounting surface of any of the composite brackets may be curved, as shown in FIG. 2a, to conform to the curvature of tooth surfaces.

I claim:
1. An orthodontic bracket comprising:
a substantially non-resilient bracket member having a base and an arch wire receiving opening formed in a surface of said bracket; and
a generally ring-shaped mounting layer of resilient material secured to said base of said bracket member and adapted to be mounted to a tooth or the like, said mounting layer having peripheral edges which extend at least adjacent to the periphery of said base of said bracket and a void space interior of said peripheral edges which underlies said base of said bracket.

2. The orthodontic bracket of claim 1, wherein said mounting layer comprises means for at least partially encircling at least a portion of the base of said bracket member.

3. The orthodontic bracket of claim 2, wherein said encircling portion of said mounting layer pressingly engages said bracket member to secure said mounting layer to said bracket member.

4. The orthodontic bracket of claim 2, wherein said mounting layer comprises a sleeve member which is slidable on said bracket member to be secured to same.

5. The orthodontic bracket of claim 1, wherein said mounting layer has an inclined surface portion for mounting said bracket to a tooth with a predetermined angular orientation relative to a tooth.

6. The orthodontic bracket of claim 1, wherein said mounting layer has a substantially flat surface portion to which said bracket member is mounted and a curved surface portion opposite said substantially flat portion for mounting to a tooth, or the like.

7. The orthodontic bracket of claim 1, wherein said ring-shaped mounting layer has a generally rectangular outer periphery.

8. The orthodontic bracket of claim 1, wherein said ring-shaped mounting layer has a generally circular outer periphery.

9. An orthodontic appliance comprising:
a substantially non-resilient first member having a base portion and means for applying an orthodontic force to a tooth, or the like; and
a generally ring-shaped mounting layer of resilient material secured to said base portion of said first member and adapted to be mounted to a tooth, or the like, said mounting layer having peripheral edges which extend at least adjacent to the periphery of said base of said first member and a void space interior of said peripheral edges which underlies said base of said first member.

10. The orthodontic appliance of claim 9, wherein said mounting layer has a curved surface for mounting to a curved surface of a tooth, or the like.

11. The orthodontic appliance of claim 9, wherein said ring-shaped resilient mounting layer has a generally rectangular outer periphery.

* * * * *